US009920034B2

(12) United States Patent
Dabros et al.

(10) Patent No.: US 9,920,034 B2
(45) Date of Patent: *Mar. 20, 2018

(54) CRYSTALLINE FORMS OF A FACTOR XIA INHIBITOR

(71) Applicant: Bristol-Myers Squibb Company, Princeton, NJ (US)

(72) Inventors: Marta Dabros, Lawrenceville, NJ (US); Chenkou Wei, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/434,507

(22) PCT Filed: Oct. 11, 2013

(86) PCT No.: PCT/US2013/064423
§ 371 (c)(1),
(2) Date: Apr. 9, 2015

(87) PCT Pub. No.: WO2014/059203
PCT Pub. Date: Apr. 17, 2014

(65) Prior Publication Data
US 2015/0266855 A1    Sep. 24, 2015

Related U.S. Application Data

(60) Provisional application No. 61/712,850, filed on Oct. 12, 2012.

(51) Int. Cl.
*C07D 401/14* (2006.01)
*A61K 31/496* (2006.01)
*A61K 9/00* (2006.01)
*A61K 9/20* (2006.01)
*A61K 9/48* (2006.01)

(52) U.S. Cl.
CPC ........... *C07D 401/14* (2013.01); *A61K 9/007* (2013.01); *A61K 9/0019* (2013.01); *A61K 9/0043* (2013.01); *A61K 9/2054* (2013.01); *A61K 9/4825* (2013.01); *A61K 9/4858* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 5,624,936 A | 4/1997 | deSolms | |
| 5,869,682 A | 2/1999 | deSolms | |
| 9,000,172 B2 * | 4/2015 | Orwat | C07D 401/14 546/146 |
| 9,192,607 B2 * | 11/2015 | Orwat | C07D 401/14 |
| 2016/0075715 A1 * | 3/2016 | Orwat | C07D 401/14 514/210.21 |

FOREIGN PATENT DOCUMENTS

| | | |
|---|---|---|
| DE | 40 34 829 A1 | 5/1992 |
| EP | 0 525 420 B1 | 5/1999 |
| EP | 1 016 663 A1 | 7/2000 |
| EP | 1 125 925 A1 | 8/2001 |
| FR | 1525186 | 5/1968 |
| FR | 7155 | 2/1970 |
| WO | WO 93/20099 | 10/1993 |
| WO | WO 96/34010 | 10/1996 |
| WO | WO 97/36891 | 10/1997 |
| WO | WO 99/15530 | 4/1999 |
| WO | WO 99/47545 | 9/1999 |
| WO | WO 99/61444 | 12/1999 |
| WO | WO 00/18733 | 4/2000 |
| WO | WO 00/40571 | 7/2000 |
| WO | WO 00/61608 | 10/2000 |
| WO | WO 01/85695 | 11/2001 |
| WO | WO 02/18369 | 3/2002 |
| WO | WO 03/011222 | 2/2003 |
| WO | WO 03/041641 | 5/2003 |
| WO | WO 2004/080971 | 9/2004 |
| WO | WO 2004/094372 | 11/2004 |
| WO | WO 2005/014533 | 2/2005 |
| WO | WO 2005/099709 | 10/2005 |
| WO | WO 2005/123050 | 12/2005 |
| WO | WO 2005/123680 | 12/2005 |
| WO | WO 2006/017295 | 2/2006 |
| WO | WO 2006/076575 | 7/2006 |
| WO | WO 2006/089005 | 8/2006 |
| WO | WO 2007/054453 | 5/2007 |

(Continued)

OTHER PUBLICATIONS

Kakkar A.P. et al., Isolation and characterization of Ciprofloxacin-HCL crystals, Drug Development and Industrial Pharmacy, 1997, pp. 1063-1067, vol. 23, No. 11, U.S.A.*

Boger, D.L. et al., "Thermal Atropisomerism of Aglucovancomycin Derivatives: Preparation of (M,M,M)- and (P,M,M)-Aglucovancomycins", J. Am. Chem. Soc., vol. 120, No. 35, pp. 8920-8926 (1998).

Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).

Chan, J.C.Y. et al., "The Characterization of Mice with a Targeted Combined Deficiency of Protein C and Factor XI", American Journal of Pathology, vol. 158, No. 2, pp. 469-479 (2001).

(Continued)

*Primary Examiner* — Emily A Bernhardt
(74) *Attorney, Agent, or Firm* — Hong Liu

(57) ABSTRACT

The instant invention provides crystalline forms of (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid and its solvates thereof; processes for the production of such crystalline forms; pharmaceutical compositions comprising such crystalline forms; and methods of treating thromboembolic disorders with such crystalline forms or such pharmaceutical compositions.

19 Claims, 11 Drawing Sheets

(56) References Cited

FOREIGN PATENT DOCUMENTS

| | | |
|---|---|---|
| WO | WO 2007/070816 | 6/2007 |
| WO | WO 2007/070818 | 6/2007 |
| WO | WO 2007/070826 | 6/2007 |
| WO | WO 2007/076431 | 7/2007 |
| WO | WO 2008/076805 | 6/2008 |
| WO | WO 2008/079836 | 7/2008 |
| WO | WO 2008/157162 | 12/2008 |
| WO | WO 2009/114677 | 9/2009 |
| WO | WO 2010/151317 | 12/2010 |
| WO | WO 2011/002520 | 1/2011 |
| WO | WO 2011/017296 | 2/2011 |
| WO | WO 2011/100401 | 8/2011 |
| WO | WO 2011/100402 | 8/2011 |
| WO | WO 2013/009527 | 1/2013 |
| WO | WO 2013/022814 | 2/2013 |
| WO | WO 2013/022818 | 2/2013 |
| WO | WO 2013/055984 | 4/2013 |
| WO | WO 2013/056034 | 4/2013 |
| WO | WO 2013/056060 | 4/2013 |
| WO | WO 2013/093484 | 6/2013 |
| WO | WO 2013/111107 | 8/2013 |
| WO | WO 2013/111108 | 8/2013 |
| WO | WO 2013/118805 | 8/2013 |
| WO | WO 2013/167669 | 11/2013 |
| WO | WO 2013/174937 | 11/2013 |
| WO | WO 2014/014050 | 1/2014 |
| WO | WO 2014/022766 | 2/2014 |
| WO | WO 2014/022767 | 2/2014 |
| WO | WO 2014/059202 | 4/2014 |
| WO | WO 2014/059214 | 4/2014 |
| WO | WO 2014/108679 | 7/2014 |
| WO | WO 2014/108685 | 7/2014 |
| WO | WO 2014/120346 | 8/2014 |
| WO | WO 2014/160668 | 10/2014 |

OTHER PUBLICATIONS

Chen, X. et al., Chapter 32: "The use of bioisosteric groups in lead optimization", Annual Reports in Medicinal Chemistry, vol. 38, pp. 333-346, Elsevier Inc., publ. (2003).

Cho, J.E. et al., "Characterization of Binding Mode for Human Coagulation Factor XI (FXI) Inhibitors", Bull. Korean Chem. Soc., vol. 34, No. 4, pp. 1212-1220 (2013).

Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).

Evans, D.A. et al., "Total Syntheses of Vancomycin and Eremomycin Aglycons", Angew. Chem. Int. Ed., vol. 37, No. 19, pp. 2700-2704 (1998).

Gailani, D., "Gene Targeting in Hemostasis, Factor XI", Frontiers in Bioscience, vol. 6, pp. 201-207 (2001).

Gailani, D. et al., "A murine model of factor XI deficiency", Blood Coagulation and Fibrinolysis, vol. 8, pp. 134-144 (1997).

Gruber, A. et al., "Factor XI-dependence of surface- and tissue factor-initiated thrombus propagation in primates", Blood, vol. 102, No. 3, pp. 953-955 (2003).

Hoffman, M., "A cell-based model of coagulation and the role of factor VIIa", Blood Reviews, vol. 17, pp. S1-S5 (2003).

Jiang, G. et al., "Highly Efficient Oxidation of Amines to Imines by Singlet Oxygen and Its Application in Ugi-Type Reactions", Organic Letters, vol. 11, No. 20, pp. 4568-4571 (2009).

Li, J.J. et al., "Tetrahydroisoquinoline 1-carboxamides as growth hormone secretagogues", Bioorganic & Medicinal Chemistry Letters, vol. 15, pp. 1799-1802 (2005).

Matafonov, A. et al., "Evidence for factor IX-independent roles for factor XIa in blood coagulation", Journal of Thrombosis and Haemostasis, vol. 11, pp. 2118-2127 (2013).

MayoClinic.com, "Pulmonary Embolism: Prevention", http://www.mayoclinic.com/health/pulmonary-embolism/DS00429/DSECTION=prevention, accessed May 20, 2013.

Meijers, J.C.M. et al., "High Levels of Coagulation Factor XI as a Risk Factor for Venous Thrombosis", The New England Journal of Medicine, vol. 342, pp. 696-701 (2000).

Minnema, M.C. et al., "Activation of Clotting Factors XI and IX in Patients with Acute Myocardial Infarction", Arterioscler. Thromb. Vasc. Biol., vol. 20, pp. 2489-2493 (2000).

Murakami, T. et al., "Evaluation of Factor XIa-$\alpha_1$-Antitrypsin in Plasma, a Contact Phase-Activated Coagulation Factor-Inhibitor Complex, in Patients with Coronary Artery Disease", Arteriosclerosis, Thrombosis, and Vascular Biology, vol. 15, No. 8, pp. 1107-1113 (1995).

Ngouansavanh, T. et al., "IBX-Mediated Oxidative Ugi-Type Multicomponent Reactions: Application to the N and C1 Functionalization of Tetrahydroisoquinoline", Angew. Chem. Int. Ed., vol. 46, pp. 5775-5778 (2007).

Rosen, E.D. et al., "FXI is Essential for Thrombus Formation Following $FeCl_3$-Induced Injury of the Carotid Artery in the Mouse", Thromb. Haemost., vol. 87, pp. 774-776 (2002).

Schumacher, W.A. et al., "Inhibition of Factor XIa as a New Approach to Anticoagulation", Arterioscler. Thromb. Vasc. Biol., vol. 30, pp. 388-392 (2010).

Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).

Schuster, I. et al., "Synthesis of 1,2,3,4-Tetrahydroisoquinoline-1-Carboxylic Acid Derivatives Via Ugi Reactions", Letters in Organic Chemistry, vol. 4, No. 2, pp. 102-108 (2007).

Schuster, I. et al., "Synthesis of 1,2,3,4-Tetrahydroisoquinoline-1-carboxylic Acid Derivatives via Ugi Reactions", Magyar Kémiai Folyóirat (Hungarian Journal of Chemistry), vol. 116, No. 3, pp. 126-130 (2010).

Walsh, P.N., "Platelets and Factor XI Bypass the Contact System of Blood Coagulation", Thrombosis and Haemostasis, vol. 82, No. 2, pp. 234-242 (1999).

Wang, X. et al., "Effects of factor IX or factor XI deficiency on ferric chloride-induced carotid artery occlusion in mice", Journal of Thrombosis and Haemostasis, vol. 3, pp. 695-702 (2005).

Wu, Y.-J. et al., "Discovery of (S,E)-3-(2-fluorophenyl)-N-(1-(3-(pyridin-3-yloxy)phenyl)ethyl)-acrylamide as a potent and efficacious KCNQ2 (Kv7.2) opener for the treatment of neuropathic pain", Bioorganic & Medicinal Chemistry Letters, vol. 23, pp. 6188-6191 (2013).

\* cited by examiner

US 9,920,034 B2

CRYSTALLINE FORMS OF A FACTOR XIA INHIBITOR

CROSS REFERENCES TO RELATED APPLICATIONS

This application is a 371 of International Application No. PCT/US2013/064423, filed on Oct. 11, 2013, which claims the benefit of U.S. Provisional Application Ser. No. 61/712,850 filed on Oct. 12, 2012 which is incorporated herein by reference.

FIELD OF THE INVENTION

The present invention relates to crystalline forms of (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid and its solvates, processes for the production thereof, pharmaceutical compositions thereof, and methods of treating thromboembolic disorders therewith.

BACKGROUND OF THE INVENTION

Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

WO 2013/056060, which is herein incorporated by reference, discloses a factor XIa inhibitor, (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid, (hereinafter referred to as "Compound (I)"):

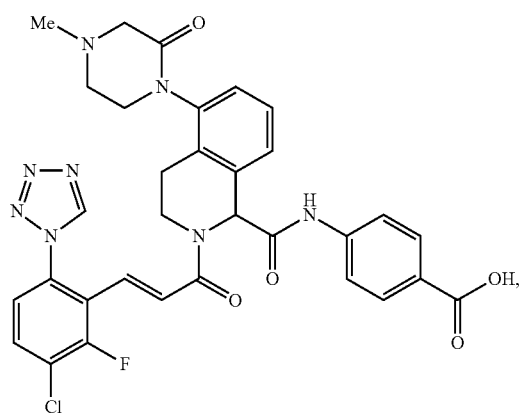

(I)

which is useful in preventing or treating thromboembolic disorders.

Treatment or prevention of the foregoing disorders may be accomplished by administering a therapeutically effective amount of Compound (I) to a human or animal subject in need of such treatment or prevention. The treatment with Compound (I) may be accomplished by its use as a single compound, as a pharmaceutical composition ingredient, or in combination with other therapeutic agents. Compound (I) may be administered by oral administration, continuous intravenous infusion, bolus intravenous administration or any other suitable route such that it preferably achieves the desired effect of preventing Factor XIa induced formation of thrombin from prothrombin.

Crystalline forms of Compound (I) have not been known to exist previously. As such, there exists a need for crystalline forms which may exhibit desirable and beneficial chemical and physical properties. There also exists a need for reliable and reproducible methods for the manufacture, purification, and formulation of Compound (I) to permit its feasible commercialization. The present invention is directed to these, as well as other important aspects.

SUMMARY OF THE INVENTION

The present invention provides crystalline forms of Compound (I), processes for the production of such forms; pharmaceutical compositions comprising such forms; and methods of treating thromboembolic disorders with such crystalline forms, or such pharmaceutical compositions. Embodiments of these crystalline forms include those characterized herein as Forms H.5-1, P13, and HCl:SA-1. The names used herein to characterize a specific form, e.g., "P13" etc., should not be considered limiting with respect to any other substance possessing similar or identical physical and chemical characteristics, but rather it should be understood that these designations are mere identifiers that should be interpreted according to the characterization information also presented herein.

These and other aspects of the invention will become more apparent from the following detailed description.

BRIEF DESCRIPTION OF THE DRAWINGS

The invention is illustrated by reference to the accompanying drawings described below.

Figure 5:
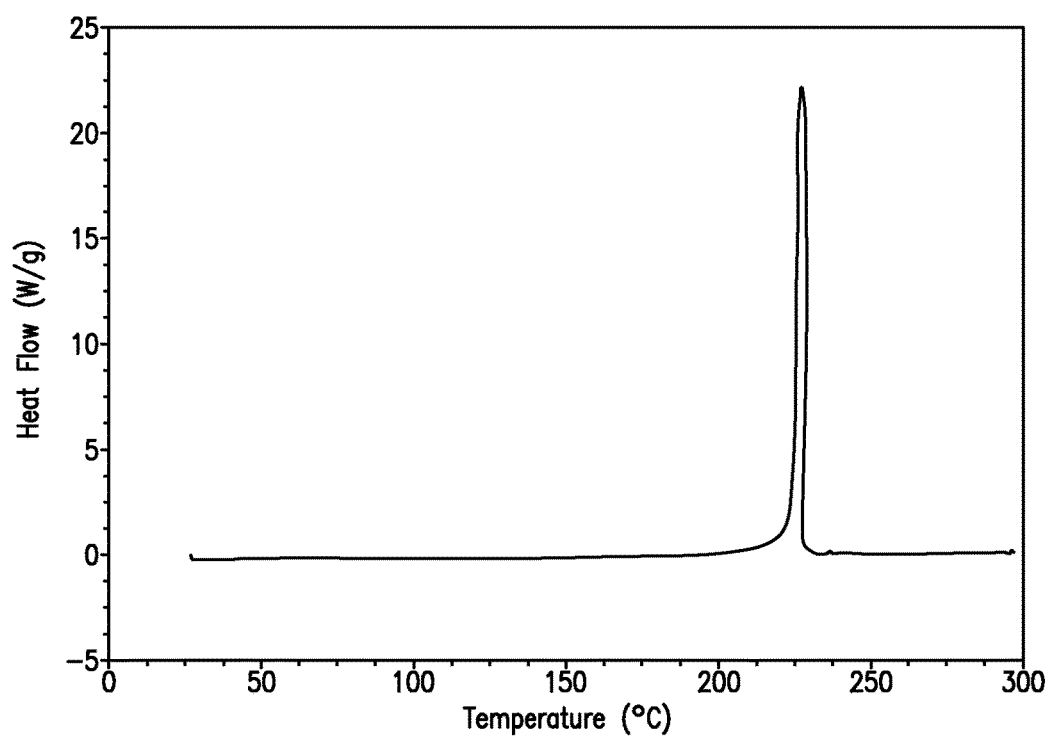

FIG. 5 is a differential scanning calorimetry thermogram of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.

Figure 6:
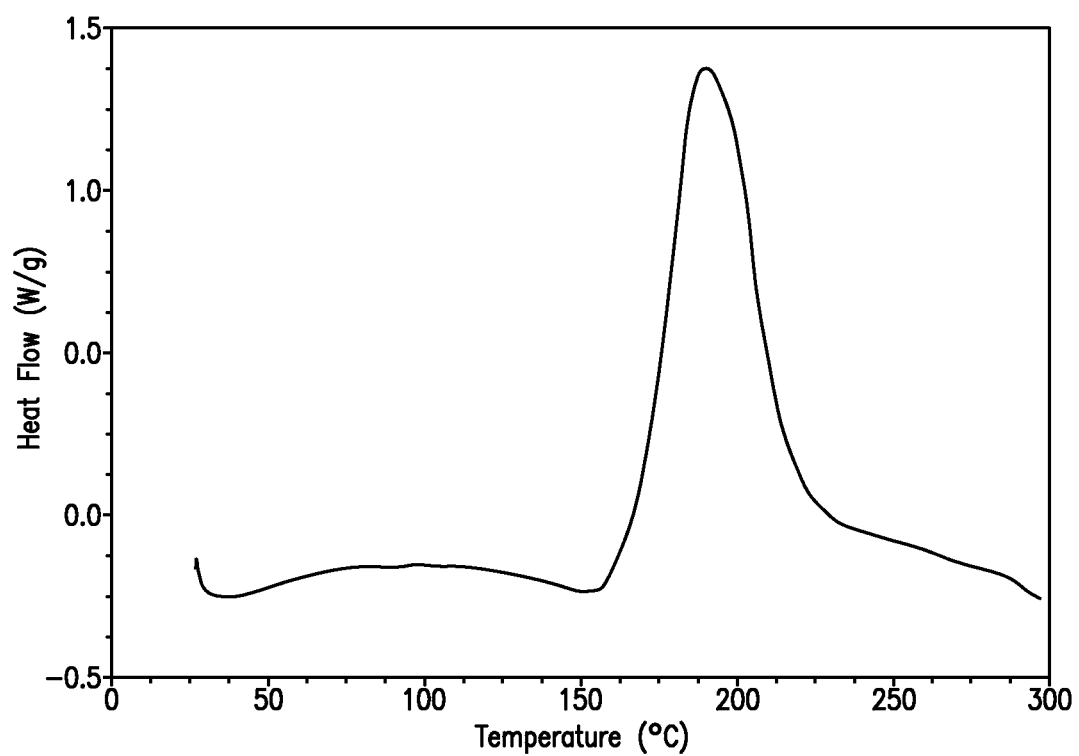

FIG. 6 is a differential scanning calorimetry thermogram of Form H.5-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.

Figure 7:
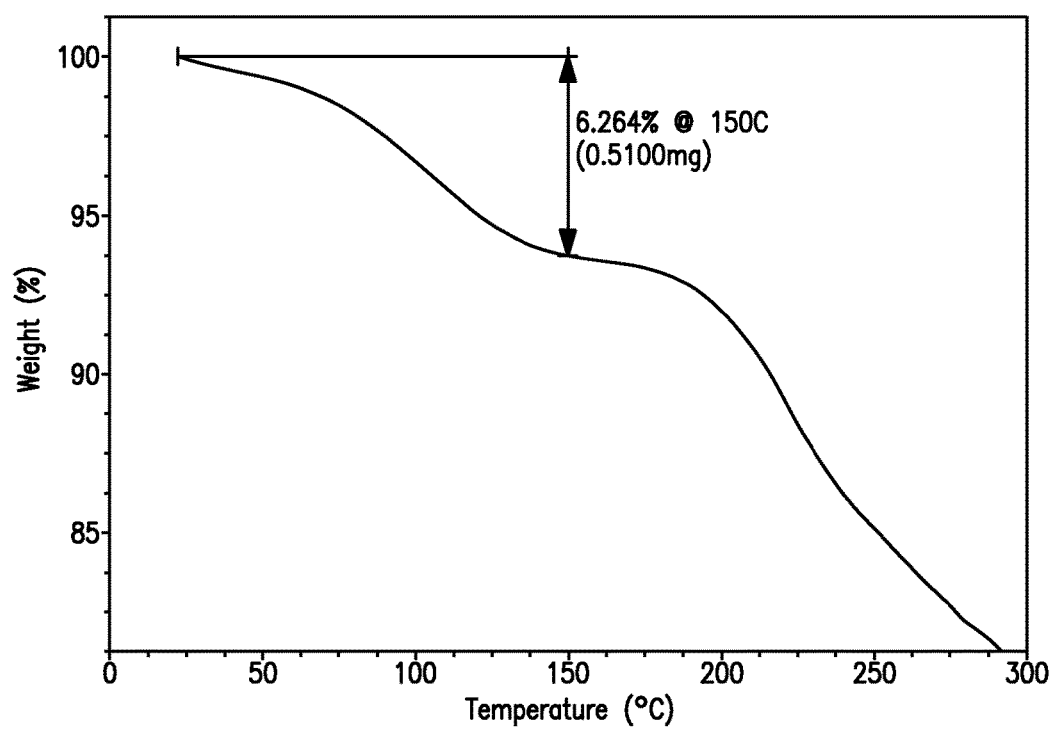

FIG. 7 is a thermogravimetric analysis thermogram of Form HCl:SA-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.

Figure 8:
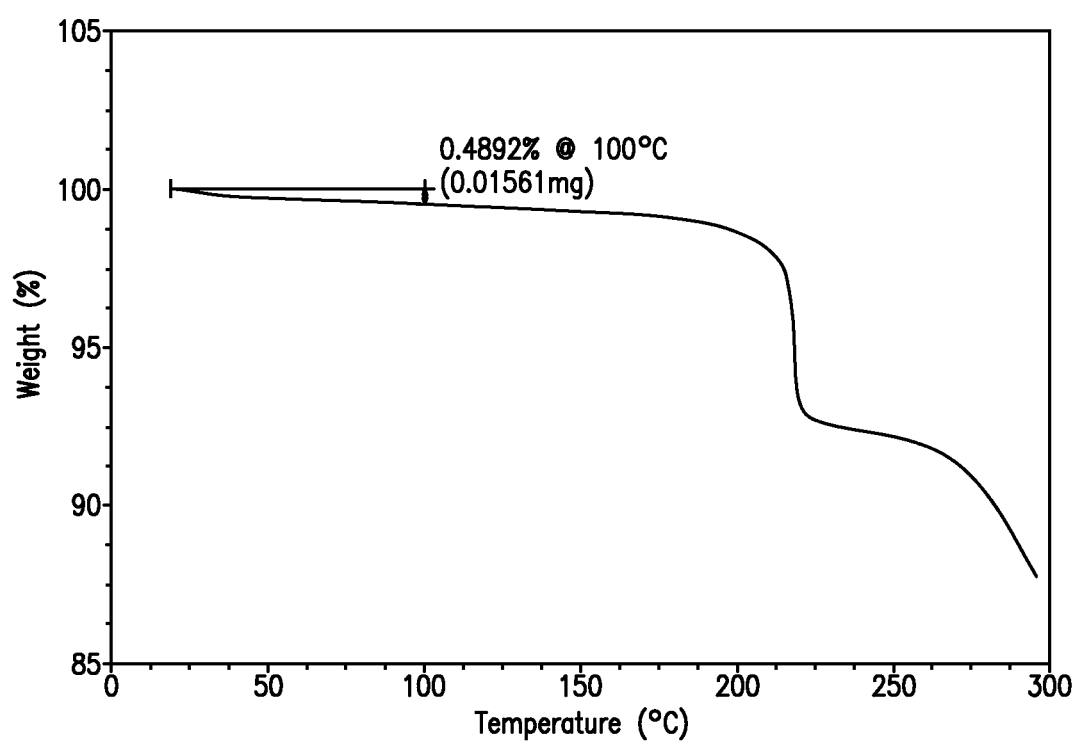

FIG. 8 is a thermogravimetric analysis thermogram of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.

Figure 9:
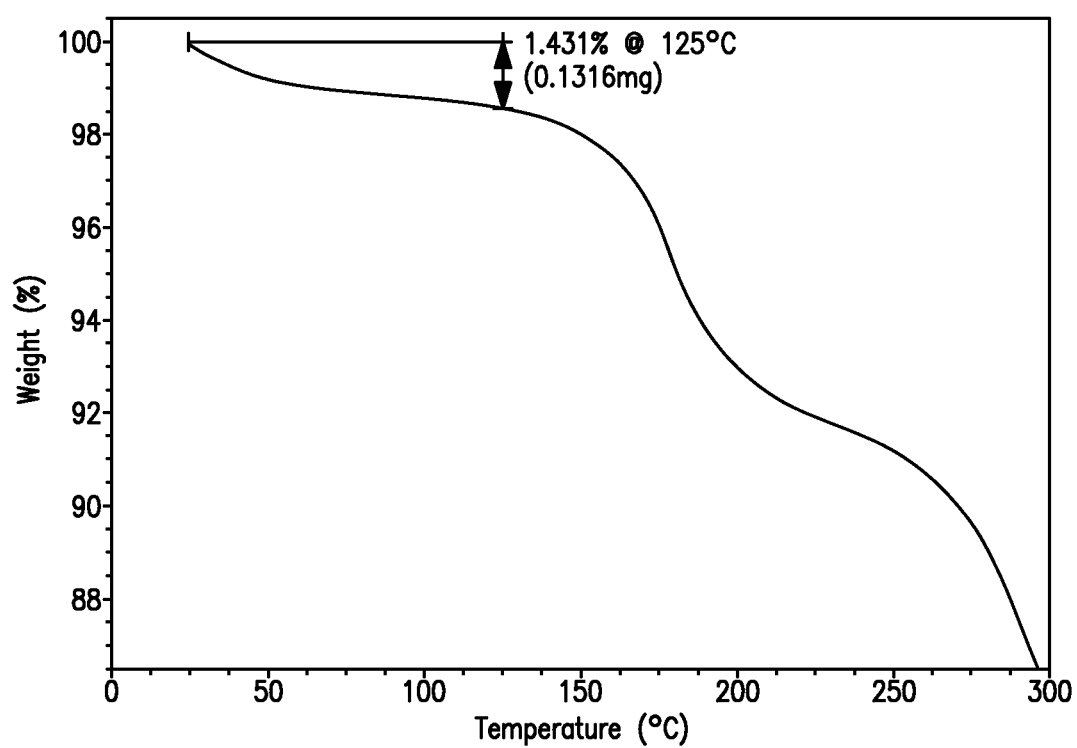

FIG. 9 is a thermogravimetric analysis thermogram of Form H.5-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.

Figure 10:
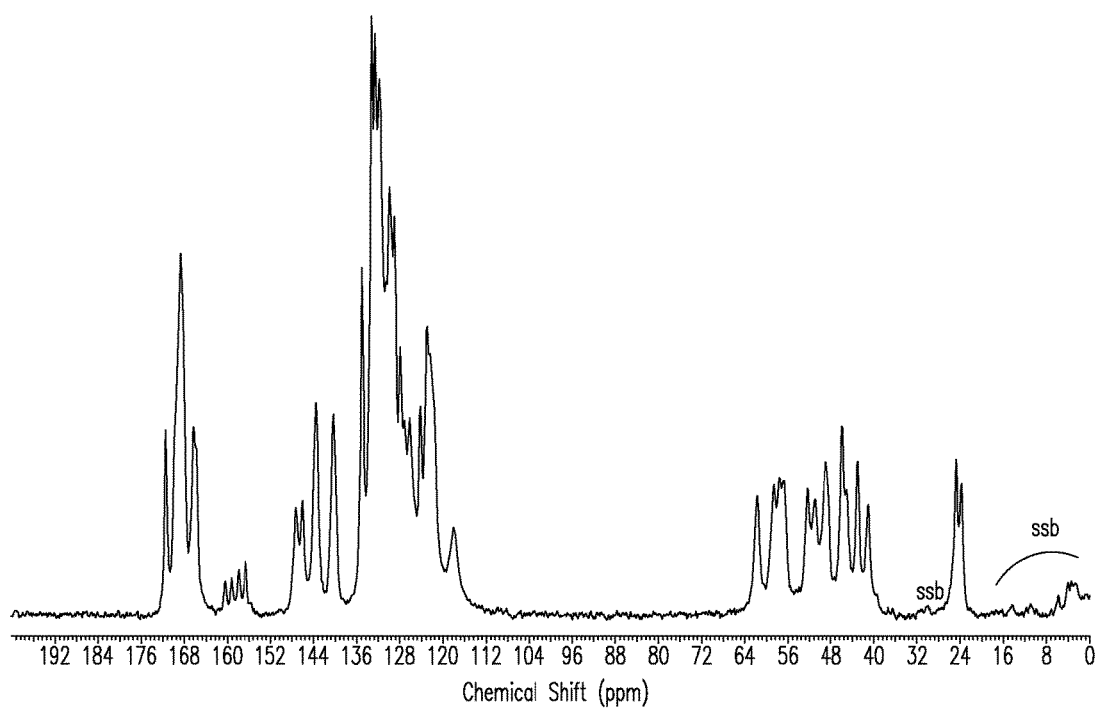

FIG. 10 is a C-13 CPMASA spectrum diagram of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid. The spinning sidebands are labeled with "ssb".

Figure 11:
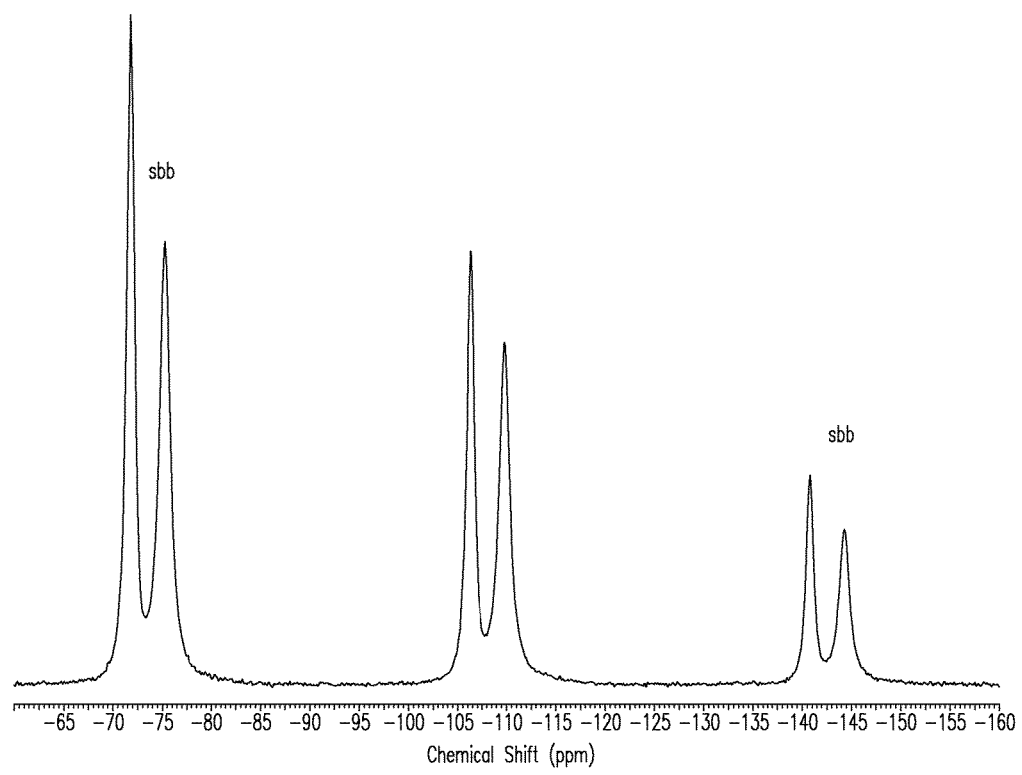

FIG. 11 is a F-19 CPMAS spectrum (with proton decoupling) diagram of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid. The spinning side bands are labeled and were confirmed by varying the spinning speed.

DETAILED DESCRIPTION OF THE INVENTION

The present invention provides, at least in part, crystalline forms of Compound (I) as a novel material, in particular in pharmaceutically acceptable form. The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, Compound (I) is in substantially pure form. The term "substantially pure", as used herein, means a compound having a purity greater than about 90% including greater than 90, 91, 92, 93, 94, 95, 96, 97, 98, and 99 weight %, and also including equal to about 100 weight % of Compound (I), based on the weight of the compound. The remaining material comprises other form(s) of the compound, and/or reaction impurities and/or processing impurities arising from its preparation. For example, a crystalline form of Compound (I) may be deemed substantially pure in that it has a purity greater than 90 weight %, as measured by means that are at this time known and generally accepted in the art, where the remaining less than 10 weight % of material comprises other form(s) of Compound (I) and/or reaction impurities and/or processing impurities.

As used herein "polymorph" refers to crystalline forms having the same chemical composition but different spatial arrangements of the molecules, and/or ions forming the crystal.

As used herein "solvate" refers to a crystalline form of a molecule, and/or ions that further comprises molecules of a solvent or solvents incorporated into the crystalline structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate.

As used herein "amorphous" refers to a solid form of a molecule, and/or ions that is not crystalline. An amorphous solid does not display an X-ray diffraction pattern with sharp maxima.

Compound (I) may be prepared using the methods taught in commonly assigned U.S. patent application Ser. No. 61/547,292. In the scheme below, Example 57 is obtained through Ugi reaction (Schuster, I. et al. (*Letters in Organic Chemistry*, 4(2):102-108(2007)). Deprotection of , Example 57 leads to Compound (I).

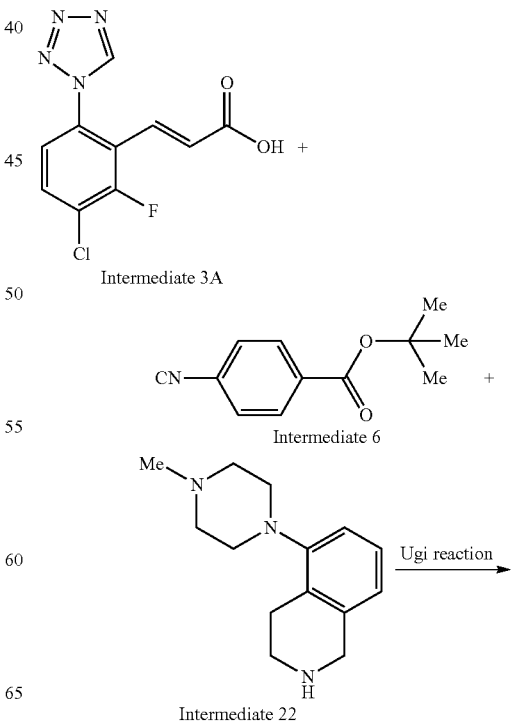

-continued

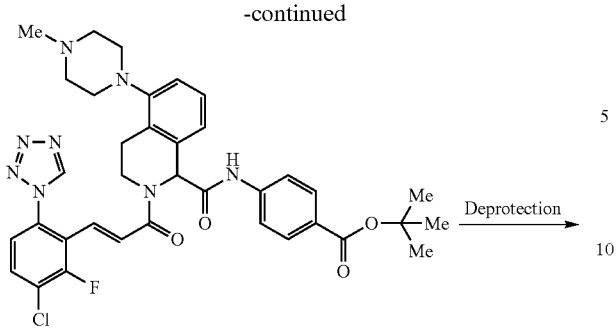

Ex. 57

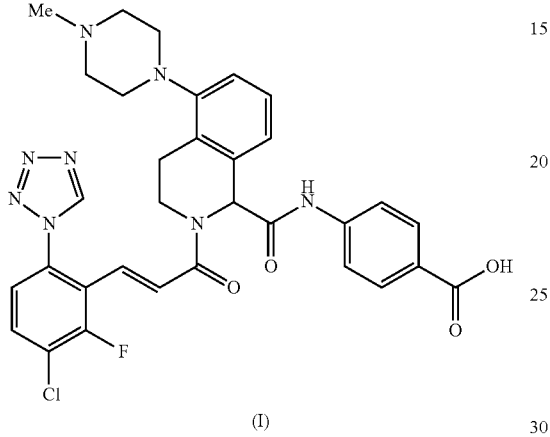

(I)

Intermediate 3A: (E)-3-(3-chloro-2-fluoro-6-(1H-tetrazol-1-yl)phenyl)acrylic acid: The synthesis of Intermediate 3A was described as Intermediate 7 in PCT International Application, WO 2009/114677 published 09/17/09.

Intermediate 6 tert-Butyl 4-isocyanobenzoate

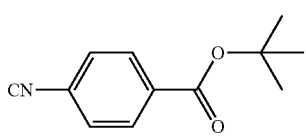

Intermediate 6A: tert-Butyl 4-formamidobenzoate: Combined tert-butyl 4-aminobenzoate (15.3 g, 79 mmol), DMAP (1.935 g, 15.84 mmol), N-methylmorpholine (15.67 mL, 143 mmol) in DCM (120 mL) and, after cooling to 0° C., slowly added formic acid (9.11 mL, 238 mmol). After stirring for 18 h, the reaction was concentrated and then partitioned with 1N HCl (100 mL) and EtOAc (200 mL). The aqueous layer was extracted with EtOAc (100 mL). The combined organic layer was washed with brine (50 mL) and dried (MgSO$_4$). The desired product was collected as yellow syrup (16 g).

Intermediate 6: To Intermediate 3A in THF (300 mL) was added TEA (33 mL, 238 mmol) and the after cooling to 0° C., POCl$_3$ (7.3 mL, 79 mmol) was slowly added and the reaction was stirred at room temperature. After 24 h, the reaction was partitioned between EtOAc (200 mL) and aqueous NaHCO$_3$ (100 mL). The aqueous layer was extracted with EtOAc (100 mL). The combined organic layer was washed with brine (50 mL) and dried (MgSO$_4$). Purification by normal phase chromatography afforded 10.4 g (64.6%) of intermediate 3 as a green solid. $^1$H NMR (400 MHz, CDCl$_3$) δ 8.02 (d, J=8.59 Hz, 2 H), 7.41 (d, J=8.34 Hz, 2 H), 1.60 (s, 9 H) ppm.

Intermediate 21 tert-butyl 4-(3,4-dihydroisoquinolin-5-yl)-3-oxopiperazine-1-carboxylate:

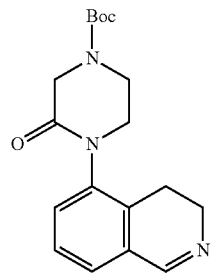 [SMILES: CC(C)(C)OC(=O)N1CCN(c2cccc3c2CCN=C3)C(=O)C1]

Intermediate 21A: tert-Butyl 4-(isoquinolin-5-yl)-3-oxopiperazine-1-carboxylate: To 5-bromoisoquinoline (0.3 g, 1.442 mmol) and tert-butyl 3-oxopiperazine-1-carboxylate (0.289 g, 1.442 mmol) was added DMSO (4 mL), 1,10-phenanthroline (0.026 g, 0.144 mmol) and K$_2$CO$_3$ (0.498 g, 3.60 mmol). The mixture was degassed for 10 min and then was added CuI (0.055 g, 0.288 mmol). The reaction was heated in a sealed tube in oil bath at 130° C. After 24 h, the reaction was incomplete. After cooling and degassing with argon, more CuI was added and heating was repeated. After 24 h, the reaction was quenched with dilute NH$_4$OH (15 mL) and extracted with EtOAc (3 ×30 mL). The combined organic layers were washed with brine (15 mL) and dried (MgSO$_4$). The crude product was purified by normal phase chromatography followed by HPLC. After partitioning with saturated NaHCO$_3$ (15 mL) and EtOAc (50 mL), organic layer was washed with brine and dried (MgSO$_4$) to afford 0.157 g (54%) of Intermediate 21A as a white solid. MS (ESI) m/z: 328 (M+H)$^+$.

Intermediate 21 was prepared from Intermediate 21A as described for Intermediate 18. MS (ESI) m/z: 330.1 (M+H)$^+$.

Intermediate 22

1-(3,4-dihydroisoquinolin-5-yl)-4-methylpiperazin-2-one:

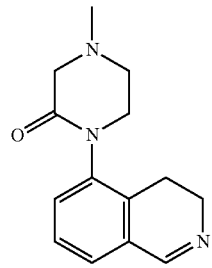 [SMILES: CN1CCN(c2cccc3c2CCN=C3)C(=O)C1]

Intermediate 22 was prepared in a similar manner as Intermediate 21 substituting 4-methylpiperazin-2-one for tert-butyl 3-oxopiperazine-1-carboxylate. MS (ESI) m/z: 244.1 (M+H)⁺.

Example 57

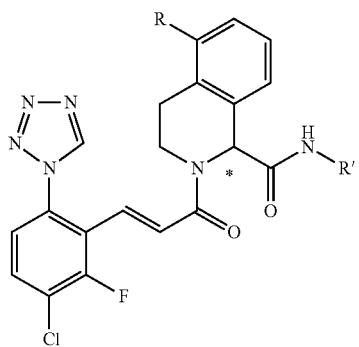

TABLE 7

| Example # | Stereo-chemistry | R | R' | M + H | RT |
|---|---|---|---|---|---|
| 57 | Racemic | (4-methyl-2-oxopiperazin-1-yl) | -4-PhCOOtBu | 715.3 | 6.82 |

Compound 183:

(R,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1- carboxamido) benzoic acid, TFA salt

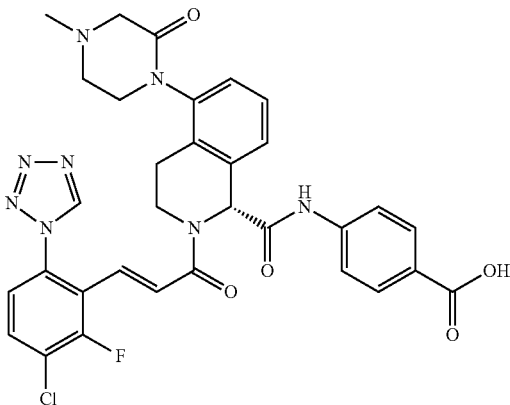 [SMILES: CN1CCN(c2cccc3c2CCN(C(=O)/C=C/c2c(-n4cnnn4)ccc(Cl)c2F)[C@H]3C(=O)Nc2ccc(C(=O)O)cc2)C(=O)C1]

Example 57 (Table 7): (E)-tert-butyl 4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoate: Intermediate 3A (0.320 g, 1.192 mmol) and Intermediate 22 (0.29 g, 1.192 mmol) were combined in a vial in EtOH (5 mL) and after 10 min., Intermediate 6 (0.315 g, 1.550 mmol) in EtOH (3mL) was added and reaction was heated at 55° C. for 24 h. The reaction was concentrated and the residue was purified by silica gel column chromatography followed by reverse phase HPLC and freeze-dried to afford 0.339 g (32.6%) of Example 57 (Table 7) as a white solid. ¹H NMR (400 MHz, MeOD) δ: 9.44 (1 H, s), 7.74-7.84 (2 H, m), 7.62-7.73 (1 H, m), 7.43-7.58 (3 H, m), 7.37 (1 H, dd, J=8.72, 1.64 Hz), 7.31 (1 H, td, J=7.83, 2.78 Hz), 7.19 (1 H, t, J=6.82 Hz), 6.98-7.11 (1 H, m), 6.79-6.94 (1 H, m), 5.80 (1 H, s), 3.94-4.20 (3 H, m), 3.84-3.95 (1 H, m), 3.62-3.80 (3 H, m), 3.53-3.64 (1 H, m), 2.99 (3 H, s), 2.92-2.96 (1 H, m), 2.61-2.77 (1 H, m), 1.47 (9 H, d, J=2.02 Hz) ppm. MS (ESI) m/z: 715.3. Analytical HPLC: RT =6.82 min.

Example 183 was prepared from Example 57 (Table 7) and isolated as the first eluting peak after chiral HPLC separation using Chiralpak AD-H, 250×30 mm, 5 μm, using 60/40 CO₂/1:1EtOH-IPA-0.1% DEA at 90 mL/min, 150 bar BP, 35° C. followed by deprotection with TFA/DCM and HPLC purification to afford 96.8 mgs (25.8%) of a white solid. ¹H NMR (400 MHz, MeOD) δ: 9.44 (1 H, s), 7.78-7.95 (2 H, m), 7.69 (1 H, td, J=8.08, 2.53 Hz), 7.44-7.60 (3 H, m), 7.27-7.41(2 H, m), 7.15-7.25 (1 H, m), 6.98-7.11 (1 H, m), 6.77-6.98 (1 H, m), 5.78-5.88 (1 H, m), 3.83-4.19 (4 H, m), 3.64-3.80 (3 H, m), 3.54-3.64 (1 H, m), 3.03 (3 H, s), 2.93-3.00 (1 H, m), 2.63-2.78 (1 H, m) ppm MS (ESI) m/z: 659.3 (M+H)⁺. Analytical HPLC: RT =4.90 min.

Example 184:

(S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid, TFA salt

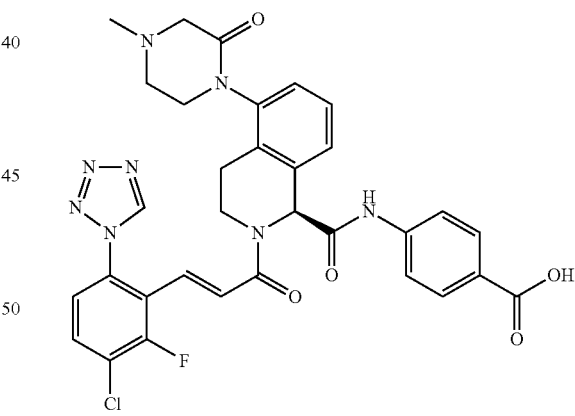

Example 184 was isolated as the second eluting enantiomer from Example 57 (Table 7) and deprotected and purified as described in in Example 183 to afford 104 mgs (27.7%) of a white solid. ¹H NMR (400 MHz, MeOD) δ: 9.45 (1 H, s), 7.79-7.92 (2 H, m), 7.64-7.74 (1 H, m), 7.44-7.62 (3 H, m), 7.27-7.43 (2 H, m), 7.15-7.24 (1 H, m), 6.97-7.12 (1 H, m), 6.72-6.90 (1 H, m), 5.77-5.88 (1 H, m), 3.82-4.17 (4 H, m), 3.53-3.82 (4 H, m), 2.99-3.03 (1 H, m), 2.98 (3 H, s), 2.60-2.77 (1 H, m) ppm. MS (ESI) m/z: 659.3 (M+H)⁺. Analytical HPLC: RT =4.94 min.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern with a simulated PXRD pattern may indicate more than one crystalline form in the sample. The simulated PXRD may be calculated from single crystal X-ray data. see Smith, D. K., A FORTRAN Program for Calculating X-Ray Powder Diffraction Patterns, Lawrence Radiation Laboratory, Livermore, Calif., UCRL-7196 (April 1963). Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated XRPD pattern. Most preferred is a crystalline form having substantially pure phase homogeneity with less than 1% of the total peak area in the experimentally measured PXRD pattern arising from the extra peaks that are absent from the simulated PXRD pattern.

The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Byrn, S. R. et al., *Solid-State Chemistry of Drugs*, Second Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility. Suitable solvents for preparing crystals include polar and nonpolar solvents.

In one method to prepare crystals, Compound (I) is suspended and/or stirred in a suitable solvent to afford a slurry, which may be heated to promote dissolution. The term "slurry", as used herein, means a saturated solution of Compound (I) and a solvent at a given temperature. Suitable solvents in this regard include, for example, polar aprotic solvents, and polar protic solvents, and nonpolar solvents, and mixtures of two or more of these.

Suitable polar aprotic solvents include, for example, dichloromethane ($CH_2Cl_2$ or DCM), tetrahydrofuran (THF), acetone, methyl ethyl ketone (MEK), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN or MeCN), dimethylsulfoxide (DMSO), propionitrile, ethyl formate, methyl acetate (MeOAc), ethyl acetate (EtOAc), isopropyl acetate (IpOAc), butyl acetate (BuOAc), t-butyl acetate, hexachloroacetone, dioxane, sulfolane, N,N-dimethylpropionamide, nitromethane, nitrobenzene and hexamethylphosphoramide.

Suitable polar protic solvents include, for example, alcohols and glycols, such as $H_2O$, methanol, ethanol, 1-propanol, 2-propanol, isopropanol (IPA), 1-butanol (1-BuOH), 2-butanol (2-BuOH), i-butyl alcohol, t-butyl alcohol, 2-nitroethanol, 2-fluoroethanol, 2,2,2-trifluoroethanol, ethylene glycol, 2-methoxyethanol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol and methyl t-butyl ether (MTBE).

Preferred solvents include, for example, acetone, $H_2O$, $CH_2Cl_2$, methanol, ethanol, MEK, IPA, and EtOAc.

Other solvents suitable for the preparation of slurries of Compound (I), in addition to those exemplified above, would be apparent to one skilled in the art, based on the present disclosure.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in "Programmed cooling of batch crystallizers", Mullin, J. W. et al., *Chemical Engineering Science*, 26:369-377 (1971). In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity of the desired crystal form or form conversions (i.e., change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, PXRD, or the like, to assure formation of the preferred crystalline form of the product. The resulting crystalline form is typically produced in an amount of greater than about 70 weight % isolated yield, but preferably greater than 90 weight % based on the weight of Compound (I) originally employed in the crystallization procedure. The product may be comilled or passed through a mesh screen to delump the product, if necessary.

Crystalline forms may be prepared directly from the reaction medium of the final process step for preparing Compound (I). This may be achieved, for example, by employing in the final process step a solvent or mixture of solvents from which Compound (I) may be crystallized. Alternatively, crystalline forms may be obtained by distillation or solvent addition techniques. Suitable solvents for this purpose include any of those solvents described herein, including protic polar solvents such as alcohols, and aprotic polar solvents such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like, by way of general guidance, the reaction solution may be distilled to about {fraction (1/10)} the original volume before solvent replacement is carried out. The reaction may be sampled and assayed to determine the extent of the reaction and the wt % product in accordance with standard process techniques. If desired, additional reaction solvent may be added or removed to optimize reaction concentration.

Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice as discussed above in connection with solvent exchange. Although the final concentration may vary depending on desired purity, recovery and the like, the final concentration of Compound (I) in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another through the use of various analytical techniques known to one of ordinary skill in the art. Such techniques include, but are not limited to, solid state nuclear magnetic resonance (SSNMR) spectroscopy, X-ray powder diffraction (PXRD), differential scanning calorimetry (DSC), and/or thermogravimetric analysis (TGA).

One of ordinary skill in the art will appreciate that an X-ray diffraction pattern may be obtained with a measurement error that is dependent upon the measurement conditions employed. In particular, it is generally known that intensities in an X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

In one aspect of the present invention, Form H.5-1 of Compound (I) may be characterized by unit cell parameters substantially equal to the following:
Cell Dimensions:
a=13.6547(3) Å
b=18.7590(3) Å
c=24.7370(5) Å
α=90°
β=90°
γ=90°
Space group: I2(1)2(1)2(1)
Molecules/asymmetric unit: 1
Density (calculated): 1.401 Mg/m$^3$
wherein measurement of the crystalline form is at a temperature of about 23° C.

In a different aspect, Form H.5-1 may be characterized by fractional atomic coordinates substantially as listed in Table 1.

In a different aspect, Form H.5-1 may be characterized by a powder X-ray diffraction pattern comprising the following 2θ values (CuKα λ=1.5418 Å): 5.9, 7.2, 12.0, 15.7, 17.2, 18.9, 20.3, 24.2, and 26.1, at room temperature.

In another aspect, Form HCl:SA-1 of Compound (I) may be characterized by unit cell parameters substantially equal to the following:
Cell Dimensions:
a=8.3746(2) Å
b=20.2236(5) Å
c=21.3099(6) Å
α=90°
β=90°
γ=90°
Space group: P2(1)2(1)2(1)
Molecules/asymmetric unit: 1
Density (calculated): 1.368 Mg/m$^3$
wherein measurement of the crystalline form is at a temperature of about 23° C.

In a different aspect, Form HCl:SA-1 may be characterized by fractional atomic coordinates substantially as listed in Table 2.

In a different aspect, Form HCl:SA-1 may be characterized by a powder X-ray diffraction pattern comprising the following 2θ values (CuKα λ=1.5418 Å): 6.0, 8.3, 8.7, 12.3, 16.2, 16.7, 17.5, 19.9, and 20.4, at room temperature.

In another aspect of the present invention, Form P13 of Compound (I) may be characterized by a powder X-ray diffraction pattern comprising the following 2θ values (CuKα λ=1.5418 Å): 8.4, 8.9, 12.7, and 17.9.

The crystalline forms of Compound (I) described herein may be formulated into pharmaceutical compositions and/or employed in therapeutic and/or prophylactic methods. These methods include, but are not limited to, the administration of the crystalline compound (I), alone or in combination with one or more other pharmaceutically active agents, including agents that may be useful in the treatment of the disorders mentioned herein.

"Therapeutically effective amount" is intended to include an amount of the crystalline forms of Compound (I) that is effective when administered alone or in combination to inhibit factor XIa. If Compound (I) is used in combination with another medication, the combination of compounds described herein may result in a synergistic combination. Synergy, as described for example by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antithrombotic effect, or some other beneficial effect of the combination compared with the individual components.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

The crystalline forms of Compound (I) and pharmaceutical compositions thereof may be useful in inhibiting Factor XIa. Accordingly, the present invention provides methods for the treatment and/or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor XIa or thrombin.

The methods preferably comprise administering to a patient a pharmaceutically effective amount of the novel crystals of the present invention, preferably in combination with one or more pharmaceutically acceptable carriers and/or excipients. The relative proportions of active ingredient and carrier and/or excipient may be determined, for example, by the solubility and chemical nature of the materials, chosen route of administration and standard pharmaceutical practice.

The crystalline forms of Compound (I) may be administered to a patient in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They may be administered alone, but generally will be administered with a pharmaceutical carrier selected on the basis of the chosen route of administration and standard pharmaceutical practice.

The dosage regimen for the crystalline forms of Compound (I) will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder. Obviously, several unit dosage forms may be administered at about the same time. The dosage of the crystalline form of Compound (I) that will be most suitable for prophylaxis or treatment may vary with the form of administration, the particular crystalline form of the compound chosen and the physiological characteristics of the particular patient under treatment. Broadly, small dosages may be used initially and, if necessary, increased by small increments until the desired effect under the circumstances is reached.

By way of general guidance, in the adult, suitable doses may range from about 0.001 to about 1000 mg/Kg body weight, and all combinations and subcombinations of ranges and specific doses therein. Preferred doses may be from about 0.01 to about 100 mg/kg body weight per day by inhalation, preferably 0.1 to 70, more preferably 0.5 to 20 mg/Kg body weight per day by oral administration, and from about 0.01 to about 50, preferably 0.01 to 10 mg/Kg body weight per day by intravenous administration. In each particular case, the doses may be determined in accordance with the factors distinctive to the subject to be treated, such as age, weight, general state of health and other characteristics which can influence the efficacy of the medicinal product. The crystalline forms of Compound (I) may be administered in a single daily dose, or the total daily dosage may be administered in divided doses of two, three, or four times daily.

For oral administration in solid form such as a tablet or capsule, the crystalline forms of Compound (I) can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms may contain a number of additional ingredients referred to herein as "excipients". These excipients include among others diluents, binders, lubricants, glidants and disintegrants. Coloring agents may also be incorporated. "Diluents", as used herein, are agents which impart bulk to the formulation to make a tablet a practical size for compression. Examples of diluents are lactose and cellulose. "Binders", as used herein, are agents used to impart cohesive qualities to the powered material to help ensure the tablet will remain intact after compression, as well as improving the free-flowing qualities of the powder. Examples of typical binders are lactose, starch and various sugars. "Lubricants", as used herein, have several functions including preventing the adhesion of the tablets to the compression equipment and improving the flow of the granulation prior to compression or encapsulation. Lubricants are in most cases hydrophobic materials. Excessive use of lubricants is undesired, however, as it may result in a formulation with reduced disintegration and/or delayed dissolution of the drug substance. "Glidants", as used herein, refer to substances which may improve the flow characteristics of the granulation material. Examples of glidants include talc and colloidal silicon dioxide. "Disintegrants", as used herein, are substances or a mixture of substances added to a formulation to facilitate the breakup or disintegration of the solid dosage form after administration. Materials that may serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmellose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

The disintegrant preferably used in the present invention is selected from the group comprising modified starches, croscarmellose sodium, carboxymethylcellulose calcium and crospovidone. A more preferred disintegrant in the present invention is a modified starch such as sodium starch glycolate.

Preferred carriers include capsules or compressed tablets which contain the solid pharmaceutical dosage forms described herein. Preferred capsule or compressed tablet forms generally comprise a therapeutically effective amount of the crystalline forms of Compound (I) and one or more disintegrants in an amount greater than about 10% by weight relative to the total weight of the contents of the capsule or the total weight of the tablet.

Preferred capsule formulations may contain the crystalline forms of Compound (I) in an amount from about 5 to about 1000 mg per capsule. Preferred compressed tablet formulations contain the crystalline forms of Compound (I) in an amount from about 5 mg to about 800 mg per tablet. More preferred formulations contain about 50 to about 200 mg per capsule or compressed tablet. Preferably, the capsule or compressed tablet pharmaceutical dosage form comprises a therapeutically effective amount of Forms H.5-1, P13 and HCl:SA-1 of Compound (I); a surfactant; a disintegrant; a binder; a lubricant; and optionally additional pharmaceutically acceptable excipients such as diluents, glidants and the like; wherein the disintegrant is selected from modified starches; croscarmellose sodium, carboxymethylcellulose calcium and crospovidone.

For oral administration in liquid form, the crystalline forms of Compound (I) can be combined with any oral, non-toxic pharmaceutically acceptable inert carrier such as ethanol, glycerol, water and the like. The liquid composition may contain a sweetening agent which to make the compositions more palatable. The sweetening agent can be selected from a sugar such as sucrose, mannitol, sorbitol, xylitol, lactose, etc. or a sugar substitute such as cyclamate, saccharin, aspartame, etc. If sugar substitutes are selected as the sweetening agent the amount employed in the compositions of the invention will be substantially less than if sugars are employed. Taking this into account, the amount of sweetening agent may range from about 0.1 to about 50% by weight, and all combinations and subcombinations of ranges and specific amounts therein. Preferred amounts range from about 0.5 to about 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used is in the range of from 200 to less than 325 mesh US Standard Screen, and all combinations and subcombinations of ranges and specific particle sizes therein.

Sterile injectable solutions may be prepared by incorporating the crystalline forms of Compound (I) in the required amounts, in the appropriate solvent, with various of the other ingredients enumerated herein, as required, followed by filtered sterilization. Generally, dispersions may be prepared by incorporating the sterilized active ingredient into a sterile vehicle which contains the dispersion medium and any other required ingredients. In the case of sterile powders for the preparation of sterile injectable solutions, the preferred methods of preparation may include vacuum drying and the freeze drying technique which may yield a powder of the active ingredient, plus any additional desired ingredient from the previously sterile-filtered solution thereof.

As would be apparent to a person of ordinary skill in the art, once armed with the teachings of the present disclosure, when dissolved, Compound (I) loses its crystalline structure, and is therefore considered to be a solution of Compound (I). All forms of the present invention, however, may be used for the preparation of liquid formulations in which Compound (I) may be, for example, dissolved or suspended. In addition, the crystalline forms of Compound (I) may be incorporated into solid formulations.

The liquid compositions may also contain other components routinely utilized in formulating pharmaceutical compositions. One example of such components is lecithin. Its use in compositions of the invention as an emulsifying agent in the range of from 0.05 to 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

The crystalline forms of Compound (I) may also be coupled with soluble polymers as targetable drug carriers. Such polymers can include polyvinylpyrrolidine pyran copolymer, polyhydroxypropylmethacrylamide-phenol, polyhydroxyethylaspartamidephenol or polyethylene oxidepolylysine substituted with palmitolyl residues. Furthermore, the crystalline Compound (I) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Gelatin capsules of the crystalline forms of Compound (I) may contain the crystalline Compound (I) and the liquid or solid compositions described herein. Gelatin capsules may also contain powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track.

In general, water, a suitable oil, saline, aqueous dextrose (glucose), and related sugar solutions and glycols, such as propylene glycol or polyethylene glycols are suitable carriers for parenteral solutions. Solutions for parenteral solutions are prepared by dissolving the crystalline Compound (I) in the carrier and, if necessary, adding buffering substances. Anti-oxidizing agents such as sodium bisulfite, sodium sulfite, or ascorbic acid either alone or combined, are suitable stabilizing agents. Citric acid and its salts and sodium EDTA may also be employed. Parenteral solutions may also contain preservatives, such as benzalkonium chloride, methyl- or propyl-paraben and chlorobutanol.

Suitable pharmaceutical carriers are described in *Remington's Pharmaceutical Sciences*, Mack Publishing Co., the disclosures of which are hereby incorporated herein by reference, in their entireties. Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient (i.e., Factor XIa inhibitor), 150 mg of lactose, 50 mg of cellulose, and 6 mg magnesium stearate.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Nasal Spray

An aqueous solution is prepared such that each 1 mL contains 10 mg of active ingredient, 1.8 mg methylparaben, 0.2 mg propylparaben and 10 mg methylcellulose. The solution is dispensed into 1 mL vials.

Lung Inhaler

A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

The preferred crystalline form of Compound (I) may serve as component (a) of this invention and can independently be in any dosage form, such as those described above, and can also be administered in various combinations, as described above. In the following description component (b) is to be understood to represent one or more agents as described herein suitable for combination therapy.

Thus, the crystalline forms of Compound (I) may be used alone or in combination with other diagnostic, anticoagulant, antiplatelet, fibrinolytic, antithrombotic, and/or profibrinolytic agents. For example, adjunctive administration of Factor XIa inhibitors with standard heparin, low molecular weight heparin, direct thrombin inhibitors (i.e., hirudin), aspirin, fibrinogen receptor antagonists, streptokinase, urokinase and/or tissue plasminogen activator may result in improved antithrombotic or thrombolytic efficacy or efficiency. The crystals described herein may be administered to treat thrombotic complications in a variety of animals, such as primates, including humans, sheep, horses, cattle, pigs, dogs, rats and mice. Inhibition of Factor XIa may be useful not only in the anticoagulant therapy of individuals having thrombotic conditions, but also when inhibition of blood coagulation may be required, such as to prevent coagulation of stored whole blood and to prevent coagulation in other biological samples for testing or storage. Thus, any Factor XIa inhibitor, including the crystalline forms of Compound (I) as described herein, can be added to or contacted with any medium containing or suspected of containing Factor XIa and in which it may be desired to inhibit blood coagulation.

The crystalline forms of Compound (I) may be used in combination with any antihypertensive agent or cholesterol or lipid regulating agent, or concurrently in the treatment of restenosis, atherosclerosis or high blood pressure. Some examples of agents that may be useful in combination with a novel form of Compound (I) according to the present invention in the treatment of high blood pressure include, for example, compounds of the following classes: beta-blockers, ACE inhibitors, calcium channel antagonists and alpha-receptor antagonists. Some examples of agents that may be useful in combination with a compound according to the invention in the treatment of elevated cholesterol levels or disregulated lipid levels include compounds known to be HMGCoA reductase inhibitors, or compounds of the fibrate class.

Accordingly, components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more that one agent, these agents may be administered together or in any order. When not administered at the same time, preferably the administration of component (a) and (b) occurs less than about one hour apart. Preferably, the route of administration of component (a) and (b) is oral. Although it may be preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

Pharmaceutical kits which may be useful for the treatment of various disorders, and which comprise a therapeutically effective amount of a pharmaceutical composition comprising a novel form of Compound (I) in one or more sterile containers, are also within the ambit of the present invention. The kits may further comprise conventional pharmaceutical kit components which will be readily apparent to those skilled in the art, once armed with the present disclosure. Sterilization of the container may be carried out using conventional sterilization methodology well known to those skilled in the art.

The present invention is further described in the following examples. All of the examples are actual examples. These examples are not to be construed as limiting the scope of the appended claims.

EXAMPLES

Example 1

Preparation of Single Crystal Forms H.5-1 and HCl:SA-1

Single Crystal X-Ray Measurement of Forms H.5-1 and HCl:SA-1

Single crystal X-ray data were collected on a Bruker AXS APEX II diffractometer with MicroStarH generator using Cu Kα radiation (λ=1.5418 Å). Indexing and processing of the measured X-ray intensity data were carried out with the APEX2 software suite (Bruker AXS, Inc., Madison, Wis., USA). The structure was solved by direct methods and refined on the basis of observed reflections using SHELXTL crystallographic package (Bruker AXS, Inc., Madison, Wis., USA). The derived atomic parameters (coordinates and temperature factors) were refined through full matrix least-squares. The function minimized in the refinements was $\Sigma_w(|F_o|-|F_c|)^2$. R is defined as $\Sigma \|F_o|-|F_c\|/\Sigma|F_o|$, while $R_w=[\Sigma_w(|F_o|-|F_c|)^2/\Sigma_w|F_o|_2]^{1/2}$, where w is an appropriate weighting function based on errors in the observed intensities. Difference Fourier maps were examined at all stages of refinement. All non-hydrogen atoms were refined with anisotropic thermal displacement parameters. Hydrogen atoms were calculated from an idealized geometry with standard bond lengths and angles and refined using a riding model.

Preparation of Single Crystal Form H.5-1

Crystal form H.5-1 (hemi-hydrate) was prepared by adding 3 mg of Compound (I) to 0.7 mL of ethyl acetate and methanol solution (1:1). Yellow prism shaped crystals were obtained after one day of slow evaporation of solution at room temperature.

Crystal Structure Data:
 Unit Cell Dimensions:
  a=13.6547(3) Å
  b=18.7590(3) Å
  c=24.7370(5) Å
  α=90°
  β=90°
  γ=90°
  Volume=6336.3(2) Å$^3$
  Crystal system: Orthorhombic
  Space group: I2(1)2(1)2(1)
  Molecules/asymmetric unit: 1
  Density (calculated)=1.401 Mg/m$^3$
wherein measurement of the crystalline form is at a temperature of about 23° C.

TABLE 1

Atomic Coordinates (×10$^4$) and Equivalent Isotropic Displacement Parameters (Å$^2$ × 10$^3$) for Compound (I) H.5-1

| | x | y | z | U(eq)* |
|---|---|---|---|---|
| Cl(1) | 1142(1) | 8638(1) | 1383(1) | 89(1) |
| F(1) | 1133(2) | 7271(1) | 862(1) | 67(1) |
| O(1) | 1102(2) | 5533(1) | −724(1) | 52(1) |
| O(2) | −779(1) | 4373(1) | 15(1) | 48(1) |
| O(3) | −4534(2) | 4606(1) | −1807(1) | 62(1) |
| O(4) | −3952(2) | 3964(2) | −2477(1) | 109(1) |
| O(5) | 3532(2) | 3748(1) | 1408(1) | 63(1) |
| N(1) | 1127(2) | 8164(1) | −968(1) | 56(1) |
| N(2) | 1654(2) | 7703(2) | −1270(1) | 73(1) |
| N(3) | 1416(3) | 7825(2) | −1768(2) | 91(1) |
| N(4) | 759(3) | 8363(2) | −1810(1) | 97(1) |
| N(5) | 1100(2) | 5019(1) | 102(1) | 35(1) |
| N(6) | −311(2) | 4095(1) | −837(1) | 46(1) |
| N(7) | 2057(2) | 3304(1) | 1616(1) | 43(1) |
| N(8) | 2218(2) | 3810(1) | 2664(1) | 57(1) |
| C(1) | 1203(2) | 8493(2) | 699(1) | 57(1) |
| C(2) | 1257(2) | 9049(2) | 342(2) | 59(1) |
| C(3) | 1267(2) | 8920(2) | −203(2) | 54(1) |
| C(4) | 1218(2) | 8232(2) | −398(1) | 46(1) |
| C(5) | 1210(2) | 7639(1) | −54(1) | 41(1) |
| C(6) | 1193(2) | 7804(2) | 496(1) | 49(1) |
| C(7) | 593(3) | 8565(2) | −1310(2) | 81(1) |
| C(8) | 1150(2) | 6900(1) | −250(1) | 42(1) |
| C(9) | 1279(2) | 6305(1) | 22(1) | 45(1) |
| C(10) | 1151(2) | 5598(1) | −230(1) | 38(1) |
| C(11) | 947(2) | 4321(1) | −154(1) | 33(1) |
| C(12) | 1229(2) | 3707(1) | 214(1) | 36(1) |
| C(13) | 1543(2) | 3812(1) | 746(1) | 35(1) |
| C(14) | 1604(2) | 4554(1) | 977(1) | 38(1) |
| C(15) | 912(2) | 5043(1) | 686(1) | 39(1) |
| C(16) | 1171(2) | 3021(1) | 5(1) | 50(1) |
| C(17) | 1412(2) | 2438(1) | 321(1) | 59(1) |
| C(18) | 1711(2) | 2537(2) | 845(1) | 55(1) |
| C(19) | 1785(2) | 3214(1) | 1053(1) | 41(1) |
| C(20) | −134(2) | 4263(1) | −318(1) | 35(1) |
| C(21) | −1221(2) | 4098(2) | −1108(1) | 42(1) |
| C(22) | −1223(3) | 3919(2) | −1650(1) | 76(1) |
| C(23) | −2072(3) | 3948(2) | −1947(1) | 78(1) |
| C(24) | −2943(2) | 4163(2) | −1711(1) | 47(1) |
| C(25) | −2940(2) | 4313(1) | −1170(1) | 40(1) |
| C(26) | −2096(2) | 4271(1) | −864(1) | 42(1) |
| C(27) | −3846(3) | 4228(2) | −2041(1) | 57(1) |
| C(28) | 2912(2) | 3605(2) | 1747(1) | 45(1) |
| C(29) | 3099(2) | 3770(2) | 2335(1) | 56(1) |
| C(30) | 1304(2) | 3112(2) | 2016(1) | 59(1) |
| C(31) | 1666(3) | 3151(2) | 2584(1) | 67(1) |
| C(32) | 2477(4) | 3923(2) | 3236(1) | 90(1) |
| O(1S) | 1006(2) | 5000 | 2500 | 50(1) |

*U(eq) is defined as one third of the trace of the orthogonalized U$^{ij}$ tensor.

Preparation of Single Crystal Form HCl:SA-1

Crystal form HCl:SA-1 (solvated mono-HCl salt) was prepared by adding 2 mg of Compound (I) to 0.7 mL of methanol, 2-butanone and butyl acetate solution (2:1:1). Yellow prism shaped crystals were obtained after one day of slow evaporation of solution at room temperature.

Crystal Structure Data:
 Unit Cell Dimensions:
  a=8.3746(2) Å
  b=20.2236(5) Å
  c=21.3099(6) Å
  α=90°
  β=90°
  γ=90°
  Volume=3609.14(16) Å$^3$
  Crystal system: Orthorhombic
  Space group: P2(1)2(1)2(1)
  Molecules/asymmetric unit: 1
  Density (calculated)=1.368 Mg/m$^3$
wherein measurement of the crystalline form is at a temperature of about 23° C.

TABLE 2

Atomic Coordinates (×10⁴) and Equivalent Isotropic Displacement Parameters ($Å^2 \times 10^3$) for Compound (I) HCl: SA-1

|  | x | y | z | U(eq)* |
|---|---|---|---|---|
| Cl(2) | 4183(3) | 7590(1) | 7388(1) | 73(1) |
| C(1) | 5350(8) | 5357(3) | -5(3) | 58(2) |
| C(2) | 5189(9) | 5113(3) | 606(3) | 62(2) |
| C(3) | 6122(9) | 4563(3) | 743(3) | 62(2) |
| C(4) | 7131(8) | 4259(3) | 322(4) | 63(2) |
| C(5) | 7186(9) | 4508(4) | -278(4) | 71(2) |
| C(6) | 6312(9) | 5055(4) | -435(3) | 72(2) |
| C(7) | 3624(12) | 6026(4) | -680(4) | 87(2) |
| C(8) | 4120(11) | 5408(4) | 1083(3) | 76(2) |
| C(9) | 3311(10) | 5137(4) | 1500(4) | 78(2) |
| C(10) | 2308(8) | 5511(3) | 1938(3) | 57(2) |
| C(11) | 481(11) | 4538(3) | 1991(4) | 79(2) |
| C(12) | -331(9) | 4186(3) | 2541(4) | 71(2) |
| C(13) | -1725(8) | 4599(3) | 2754(3) | 56(2) |
| C(14) | -1568(8) | 5294(3) | 2755(3) | 51(2) |
| C(15) | 41(8) | 5604(3) | 2612(3) | 50(2) |
| C(16) | -3161(9) | 4326(3) | 2946(3) | 59(2) |
| C(17) | -4444(9) | 4719(4) | 3106(3) | 69(2) |
| C(18) | -4286(9) | 5400(4) | 3088(4) | 70(2) |
| C(19) | -2842(8) | 5689(3) | 2911(3) | 60(2) |
| C(20) | 938(8) | 5679(3) | 3244(3) | 54(2) |
| C(21) | 971(8) | 6440(3) | 4151(3) | 53(2) |
| C(22) | 2064(8) | 6122(3) | 4526(3) | 61(2) |
| C(23) | 2282(8) | 6336(4) | 5147(3) | 62(2) |
| C(24) | 1416(8) | 6856(3) | 5378(3) | 54(2) |
| C(25) | 315(9) | 7169(3) | 4999(3) | 64(2) |
| C(26) | 103(9) | 6969(3) | 4387(3) | 62(2) |
| C(27) | 1629(9) | 7122(4) | 6032(3) | 67(2) |
| C(28) | -4232(14) | 3275(4) | 2493(4) | 101(3) |
| C(29) | -3869(13) | 2532(4) | 2464(4) | 96(3) |
| C(30) | -2699(9) | 2550(3) | 3483(3) | 66(2) |
| C(31) | -2625(9) | 3285(3) | 3458(3) | 60(2) |
| C(32) | -5588(10) | 2286(4) | 3384(5) | 102(3) |
| Cl(1) | 8255(3) | 3595(1) | 563(1) | 95(1) |
| F(1) | 6062(6) | 4310(2) | 1340(2) | 93(1) |
| N(1) | 4510(8) | 5920(3) | -180(3) | 71(2) |
| N(2) | 4579(11) | 6492(3) | 148(3) | 96(2) |
| N(3) | 3701(14) | 6911(4) | -149(5) | 123(3) |
| N(4) | 3089(12) | 6638(4) | -679(4) | 116(3) |
| N(5) | 1037(7) | 5207(2) | 2179(2) | 58(1) |
| N(6) | 645(7) | 6263(2) | 3524(2) | 58(1) |
| N(7) | -3312(7) | 3606(2) | 2977(3) | 60(1) |
| N(8) | -3972(7) | 2250(3) | 3097(3) | 68(2) |
| O(1) | 2620(6) | 6081(2) | 2096(2) | 70(1) |
| O(2) | 1744(6) | 5235(2) | 3465(2) | 63(1) |
| O(3) | 971(7) | 7602(3) | 6233(2) | 91(2) |
| O(4) | 2705(7) | 6777(2) | 6357(2) | 81(2) |
| O(5) | -1867(7) | 3575(2) | 3864(3) | 80(2) |
| O(1S) | 8222(7) | 5981(2) | 1227(2) | 70(1) |
| O(2S) | 489(6) | 5435(3) | 69(3) | 103(2) |
| O(3SB) | 9450(30) | 6486(13) | 631(17) | 126(8) |
| O(3SA) | 9170(30) | 6463(11) | 1022(13) | 136(7) |
| O(3SC) | 9560(30) | 6237(13) | 140(14) | 137(8) |

*U(eq) is defined as one third of the trace of the orthogonalized $U^{ij}$ tensor.

Example 2

Preparation of Form HCl:SA-1

Figure 1:
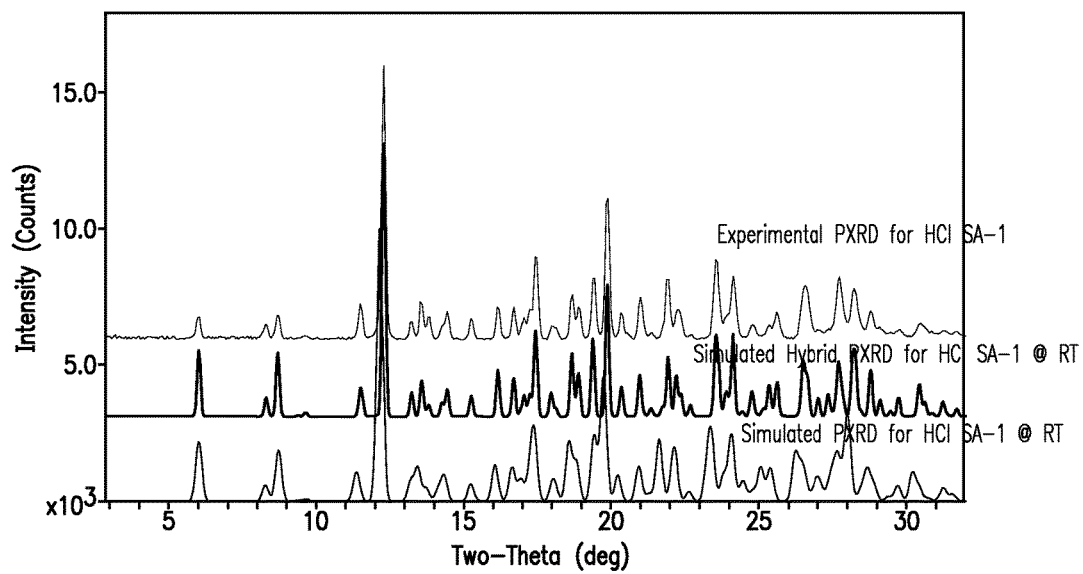
FIG. 1 shows the observed and calculated (room temperature) powder X-ray diffraction patterns (CuKα λ=1.5418 Å) of Form HCl:SA-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.
Figure 4:
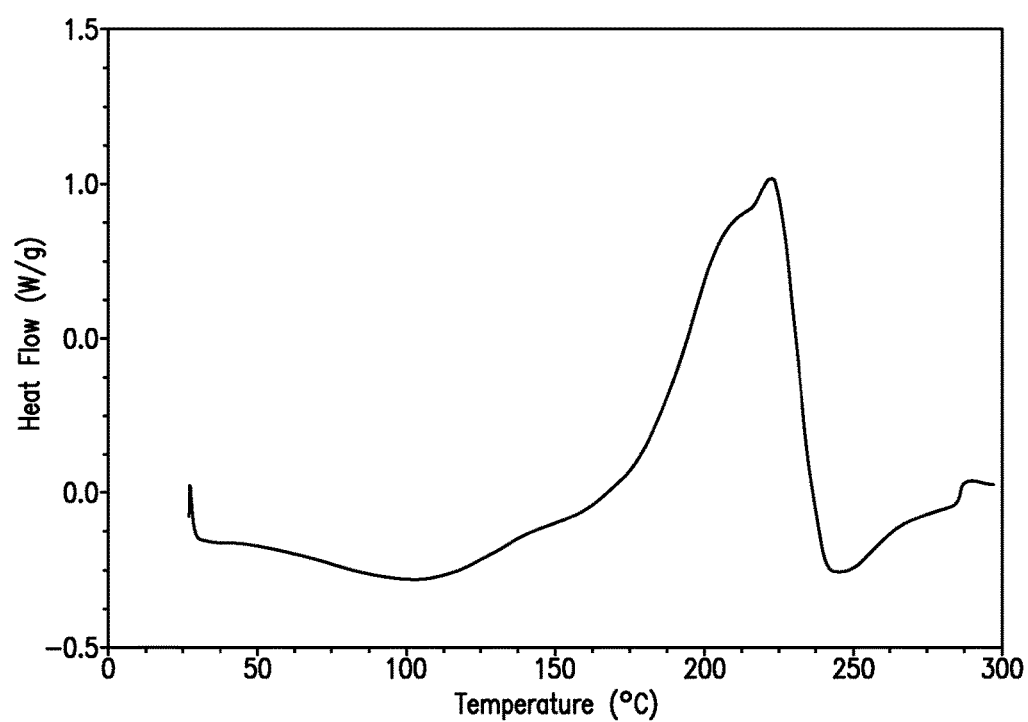
FIG. 4 is a differential scanning calorimetry thermogram of Form HCl:SA-1 of crystalline (S,E)-4-(2-(3-(3-chloro-2- fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.

In a reactor, 415 g of dried crude Compound (I) was dissolved in 9.0 kg of a solution of 200 Proof ethanol and purified water (70:30). The batch was heated to 66° C. and polish filtered into another reactor. 708 g of the Ethanol/water solution was used to rinse the first reactor and transferred through the filter into the reactor containing the solution mixture. The temperature of the batch was lowered to 50° C. and 2.24 g of Compound (I) was added in one portion. After 30 minutes the batch was cooled to 0° C. over 4 h and allowed to age at that temperature for 60 minutes. The temperature of the batch was then increased to 50° C. over a 2 h period and held for an additional 30 minutes. Again, the batch temperature was then reduced to 0° C. over 4 h and 2.9 L of 200 Proof ethanol was added to the batch. The slurry was filtered at 0° C. and the wet cake was washed twice with 0.9 L of 200 Proof ethanol. The wet cake was dried in a vacuum oven at 40° C. for a minimum of 12 h and until the ethanol content is <6.6 weight percent. The bulk material obtained was characterized by PXRD (GADDS-NB), DSC and TGA analyses and the results are shown in FIGS. 1, 4, and 7.

PXRD data were obtained using a Bruker C2 GADDS. The radiation was Cu Kα (40 KV, 40 mA). The sample-detector distance was 15 cm. Powder samples were placed in sealed glass capillaries of 1 mm or less in diameter; the capillary was rotated during data collection. Data were collected approximately for $2 \leq 2\theta \leq 35°$ with a sample exposure time of at least 1000 seconds. The resulting two-dimensional diffraction arcs were integrated to create a traditional 1-dimensional PXRD pattern with a step size of 0.05 degrees 2θ in the approximate range of 2 to 35 degrees 2θ.

"Hybrid" simulated powder X-ray patterns were generated as described in the literature (Yin. S. et al., *American Pharmaceutical Review*, 6(2):80 (2003)). The room temperature cell parameters were obtained by performing a cell refinement using the CellRefine.xls program. Input to the program includes the 2-theta position of ca. 10 reflections, obtained from the experimental room temperature powder pattern; the corresponding Miller indices, hkl, were assigned based on the single-crystal data collected for an isostructural analog. A crystal structure for the molecule of interest was generated in a two step process: (1) by replacing the analog molecule in the experimental analog crystal structure with the molecule of interest. This step fixes the orientation and position of the molecule of interest in the unit cell of the analog compound; (2) Inserting the molecule of interest into the room temperature cell obtained from the experimental PXRD of the molecule of interest, as described above. In this step, the molecules are inserted in a manner that retains the size and shape of the molecule and the position of the molecules with respect to the cell origin, but, allows intermolecular distances to expand/contract with the cell. A new (hybrid) PXRD was calculated (by either of the software programs, Alex or LatticeView) based on the crystal structure generated as described above.

DSC (Open Pan)

DSC experiments were performed in a TA INSTRUMENTS® model Q2000, Q1000 or 2920. The sample (about 2-10 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

TGA (Open Pan)

TGA experiments were performed in a TA INSTRUMENTS® model Q5000, Q500 or 2950. The sample (about 4-30 mg) was placed in a platinum pan previously tared. The weight of the sample was measured accurately and recorded to a thousandth of a milligram by the instrument. The furnace was purged with nitrogen gas at 100 mL/min. Data were collected between room temperature and 300° C. at 10° C./min heating rate.

Example 3

Preparation of Form H.5-1

Figure 2:
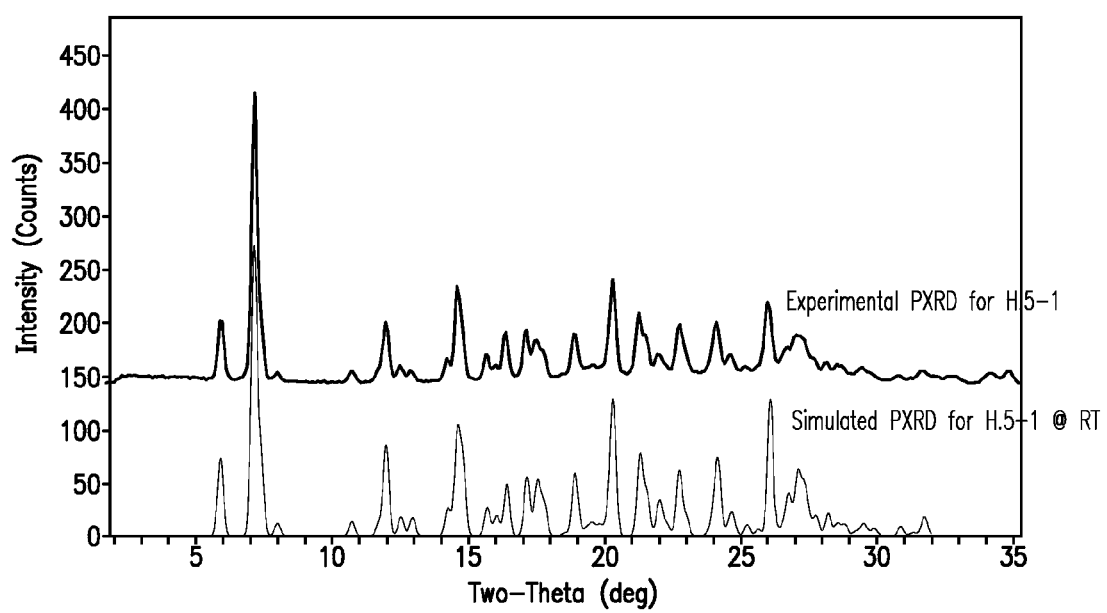
FIG. 2 shows the observed and calculated (room temperature) powder X-ray diffraction patterns (CuKα λ=1.5418 Å) of Form H.5-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.
Figure 3:
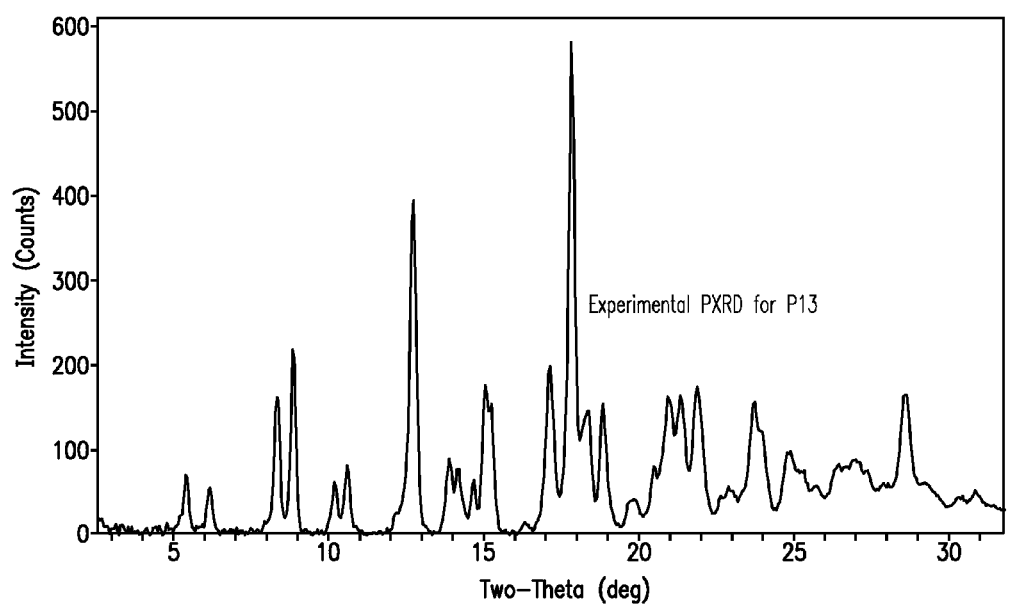
FIG. 3 shows the observed powder X-ray diffraction patterns (CuKα λ=1.5418 Å) of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.

60 g of dried crude Compound (I) was dissolved in 240 mL of 200 Proof ethanol (4 mL/g) at room temperature. In one portion, 13.25 mL of triethylamine (1.1 equiv) was added and the reaction mixture was aged for a minimum of 3 h. The solution was cooled to 0° C. and remained at that temperature for a minimum of 30 min. The slurry was filtered and the solids were washed with 30 mL of 200 Proof ethanol (0.5 mL/g). The wet cake was dissolved in 600 mL of purified water (10 mL/g) and stirred for a minimum of 30 min at room temperature. The slurry was filtered and the solids were washed with 120 mL of purified water (2 mL/g) and then 180 mL of purified water (3 mL/g). The wet cake was dried at 45° C. under vacuum for a minimum of 12 h. The obtained crystal was subjected to further analyses and the results are shown in FIGS. 2, 6, and 9.

Example 4

Preparation of Form P13

A slurry 6.8 g of Example 1 in 33 mL of methanol (4.9 mL/g) and 102 mL of dichlormethane (15 mL/g) was heated to 40° C. and became a homogeneous solution. Atmospheric distillation with constant volume addition of dichloromethane (136 mL) was performed over the next hour with batch temperature maintained at 40° C. The batch was cooled to 15° C., and a solvent swap from dichloromethane/methanol solution to ethyl acetate at constant volume was initiated under reduced pressure (150 mmHg). The batch temperature was raised to 37° C., 400 mL of ethyl acetate was used to complete the solvent swap with a remainder of 136 mL of ethyl acetate in the reactor. The batch was cooled to 20° C. and allowed to age for 12 h. The slurry was filtered and the resulting wet cake was dried at 50° C. under reduced pressure for 6 h. The dried material was subjected to PXRD, Solid-State Nuclear Magnetic Resonance (SSNMR) and the results are shown in FIGS. 3, 5, 8, 10, and 11.

Carbon cross polarization magic angle spinning (CP-MAS) solid state NMR experiments were conducted on a Bruker AV III instrument operating at a proton frequency of 400.1 MHz. Solid samples were spun at 13 KHz in a 4 mm $ZrO_2$ rotor. The contact time was 3 miliseconds and was ramped on the proton channel from 50 to 100%. (Bennett, A. E. et al., *J. Chem. Phys.*, 103:6951 (1995); Metz, G. et al., *J. Magn. Reson. A*, 110:219-227 (1994)). The relaxation delay was maintained at 20 seconds. Proton decoupling was applied using a TPPM sequence with a 4 microsecond pulse (62.5 KHz nominal band width). The spectral sweep width was 300 ppm centered at 100 ppm. 4096 data points were acquired and zero filled to 8192 prior to apodization with 20 Hz line broadening. Typically 2096 free induction decays were coadded. The spectra were referenced indirectly to TMS using 3-methylglutaric acid (Barich, D. et al., *Solid State Nuc. Mag. Res.*, 30:125-129 (2006)). Approximately 70 mg of sample was used for each experiment.

Fluorine magic angle spinning (MAS) solid state and cross polarization magic angle spinning (CPMAS) solid state NMR experiments were conducted on a Bruker AV III instrument operating at a proton frequency of 400.1 MHz. Solid samples were spun at 11, 12 and 13 KHz in a 4 mm $ZrO_2$ rotor. Data collected at 13 KHz is reported. The relaxation delay was maintained at 30 seconds for the MAS and 5 seconds for the CPMAS experiments. Proton decoupling was applied to the CPMAS experiments using a TPPM sequence with a 4 microsecond pulse (62.5 KHz nominal band width). The spectral sweep width was 500 ppm centered at −100 ppm. 4096 data points were acquired and zero filled to 8192 prior to apodization with 20 Hz line broadening. Typically 256 free induction decays were coadded. The spectra were referenced indirectly to $CCl_3F$ using PTFE (at −122 ppm).

Various crystalline forms of Compound (I) and its solvates were prepared and their characteristic peak positions are tabulated in Table 3. The unit cell data and other properties for these examples are tabulated in Tables 4-6. The unit cell parameters were obtained from single crystal X-ray crystallographic analysis. A detailed account of unit cells can be found in Chapter 3 of Stout et al., *X-Ray Structure Determination: A Practical Guide*, MacMillian (1968).

TABLE 3

Characteristic Diffraction Peak Positions (degrees 2θ ± 0.1) @ RT, Based on a High Quality Pattern Collected with a Diffractometer (CuKα) with a Spinning Capillary with 2θ Calibrated with a NIST Other Suitable Standard

| HCl: SA-1 | Free Base H.5-1 | Free Base P13 |
|---|---|---|
| 6.0 | 5.9 | 8.4 |
| 8.3 | 7.2 | 8.9 |
| 8.7 | 12.0 | 12.7 |
| 12.3 | 15.7 | 17.9 |
| 16.2 | 17.2 | |
| 16.7 | 18.9 | |
| 17.5 | 20.3 | |
| 19.9 | 24.2 | |
| 20.4 | 26.1 | |

TABLE 4

Cell Parameters for Single Crystal (Input) and Hybrid (Refined) for Form HCl: SA-1

| Cell Parameter | Input | Refined |
|---|---|---|
| a (Å) | 8.3746 | 8.2562 |
| b (Å) | 20.2236 | 20.2918 |
| c (Å) | 21.3099 | 21.2423 |
| α° | 90 | 90 |
| β° | 90 | 90 |
| γ° | 90 | 90 |
| Volume (Å³) | 3609.14 | 3558.77 |

TABLE 5

Carbon Chemical Shifts (Referenced to External TMS) for P13

| No. | (ppm) |
|---|---|
| 1 | 23.8 |
| 2 | 24.8 |
| 3 | 41.1 |
| 4 | 43.0 |
| 5 | 45.1 |
| 6 | 45.9 |
| 7 | 48.5 |
| 8 | 49.0 |
| 9 | 51.0 |
| 10 | 52.4 |
| 11 | 56.8 |
| 12 | 57.6 |
| 13 | 58.6 |
| 14 | 61.7 |
| 15 | 118.1 |

TABLE 5-continued

Carbon Chemical Shifts (Referenced to External TMS) for P13

| No. | (ppm) |
|---|---|
| 16 | 121.7 |
| 17 | 122.0 |
| 18 | 122.5 |
| 19 | 123.0 |
| 20 | 124.2 |
| 21 | 126.1 |
| 22 | 127.1 |
| 23 | 127.9 |
| 24 | 129.0 |
| 25 | 129.9 |
| 26 | 130.5 |
| 27 | 130.6 |
| 28 | 131.8 |
| 29 | 132.6 |
| 30 | 133.3 |
| 31 | 135.0 |
| 32 | 139.9 |
| 33 | 140.4 |
| 34 | 143.6 |
| 35 | 146.1 |
| 36 | 147.3 |
| 37 | 156.6 |
| 38 | 157.9 |
| 39 | 159.2 |
| 40 | 160.4 |
| 41 | 165.7 |
| 42 | 166.3 |
| 43 | 168.7 |
| 44 | 169.7 |
| 45 | 171.4 |

TABLE 6

F-19 Chemical Shifts (Referenced to External CCl$_3$F) for P13

| No. | (ppm) |
|---|---|
| 1 | −109.8 |
| 2 | −106.3 |

Numerous modifications and variations of the present invention are possible in light of the above teachings. It is therefore to be understood that within the scope of the appended claims, the invention may be practiced otherwise than as specifically described herein.

What is claimed is:

1. A crystalline mono-HCl salt form, Form HCl:SA-1, of (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid, which is characterized by a powder X-ray diffraction pattern substantially in accordance with that shown in FIG. 1.

2. The crystalline form according to claim 1 having a powder X-ray diffraction pattern comprising four or more 2θ values (CuKα λ=1.5418 Å): 6.0, 8.3, 8.7, 12.3, 16.2, 16.7, 17.5, 19.9, and 20.4.

3. The crystalline form according to claim 1, which is characterized by unit cell parameters substantially equal to the following:
Cell dimensions:
a=8.3746(2) Å
b=20.2236(5) Å
c=21.3099(6) Å
α=90°
β=90°
γ=90°
Space group: P2(1)2(1)2(1)
Molecules/asymmetric unit: 1
wherein measurement of the crystalline form is at a temperature of about 23° C.

4. The crystalline form according to claim 3, which is characterized by fractional atomic coordinates substantially as listed in Table 2.

5. The crystalline form according to claim 1, which is characterized by unit cell parameters substantially as listed in Table 4.

6. A crystalline hemi-hydrate form, Form H.5-1, of (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid, which is characterized by a powder X-ray diffraction pattern substantially in accordance with that shown in FIG. 2.

7. The crystalline form according to claim 6 having a powder X-ray diffraction pattern comprising four or more 2θ values (CuKα λ=1.5418 Å): 5.9, 7.2, 12.0, 15.7, 17.2, 18.9, 20.3, 24.2, and 26.1.

8. The crystalline form according to claim 6, which is characterized by unit cell parameters substantially equal to the following:
Cell dimensions:
a=13.6547(3) Å
b=18.7590(3) Å
c=24.7370(5) Å
α=90°
β=90°
γ=90°
Space group: I2(1)2(1)2(1)
Molecules/asymmetric unit: 1
Density (calculated): 1.401 Mg/m$^3$
wherein measurement of the crystalline form is at a temperature of about 23° C.

9. The crystalline form according to claim 8, which is characterized by fractional atomic coordinates substantially as listed in Table 1.

10. A crystalline form, Form P13, of (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid, which is characterized by a powder X-ray diffraction pattern substantially in accordance with that shown in FIG. 3.

11. The crystalline form according to claim 10 having a powder X-ray diffraction pattern comprising four or more 2θ values (CuKα λ=1.5418 Å): 8.4, 8.9, 12.7, and 17.9.

12. The crystalline form according to claim 1, in substantially pure form.

13. The Form according to claim 12, wherein substantially pure is greater than 90 percent pure.

14. A pharmaceutical composition comprising a therapeutically effective amount of a crystalline hemi-hydrate form, Form H.5-1, of claim 6 and a pharmaceutically acceptable carrier.

15. A pharmaceutical composition comprising a therapeutically effective amount of a crystalline form, Form P13, of claim 10, and a pharmaceutically acceptable carrier.

16. A pharmaceutical composition comprising a therapeutically effective amount of a crystalline mono-HCl salt Form, Form HCl:SA-1, of claim 1, and a pharmaceutically acceptable carrier.

17. A method for treating a thromboembolic disorder, comprising: administering to a patient in need thereof a therapeutically effective amount of crystalline Form according to claim 16.

18. A method according to claim 17, wherein the thromboembolic disorder is selected from the group consisting of arterial cardiovascular thromboembolic disorders, venous cardiovascular thromboembolic disorders, and thromboembolic disorders in the chambers of the heart.

19. A method according to claim 17, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

\* \* \* \* \*